United States Patent [19]

Aeby

[11] Patent Number: 5,692,902

[45] Date of Patent: Dec. 2, 1997

[54] SET OF INSTRUMENTS FOR THE BORING OF RADICULAR DENTAL CANALS

[75] Inventor: François Aeby, Chemin du Temple, Switzerland

[73] Assignee: Maillefer Instruments S.A., Switzerland

[21] Appl. No.: 557,486

[22] Filed: Nov. 14, 1995

[30] Foreign Application Priority Data

Mar. 24, 1995 [CH] Switzerland ............... 851/95

[51] Int. Cl.⁶ .................................................. A61C 5/02
[52] U.S. Cl. ................................................... 433/102
[58] Field of Search ........................... 433/102, 224, 433/165

[56] References Cited

U.S. PATENT DOCUMENTS

| | | | |
|---|---|---|---|
| 1,067,015 | 7/1913 | Fowler | 433/102 |
| 1,307,446 | 6/1919 | Kerr | 433/102 |
| 4,260,379 | 4/1981 | Groves et al. | 433/102 |
| 4,443,193 | 4/1984 | Roane | 433/102 |
| 4,934,934 | 6/1990 | Arpaio, Jr. et al. | 433/102 |
| 4,971,556 | 11/1990 | Ritano | 433/102 |
| 5,017,138 | 5/1991 | Schilder | 433/102 |
| 5,380,200 | 1/1995 | Heath et al. | 433/102 |
| 5,464,362 | 11/1995 | Heath et al. | 433/102 |

FOREIGN PATENT DOCUMENTS

| | | |
|---|---|---|
| 5011255 | 2/1992 | European Pat. Off. . |
| A86648 | 9/1920 | Switzerland . |

*Primary Examiner*—Cary E. O'Connor
*Attorney, Agent, or Firm*—Silverman, Cass & Singer, Ltd.

[57] ABSTRACT

The central part of the instruments of the boring set, prior to the portion having the cutting edges, has a section of a polygonal shape. The lateral faces of the central part are either convex, for the instruments of small diameter, plane for the instruments of middle diameter and concave for the instruments of largest diameter, in such a way that the curve of the bending moments of the instruments of the set is substantially rectilinear. Thus the variation of the bending moments of the instruments is linear, while, in previously known sets of instruments, the curve is exponential. Hence, the flexibility of the instruments of the set is satisfactory for the entire set of instruments, while; in the known conventional sets, if previously flexibility of the small instruments of the set is satisfactory, the instruments of largest diameter will be too rigid, and vice versa.

2 Claims, 1 Drawing Sheet

5,692,902

SET OF INSTRUMENTS FOR THE BORING OF RADICULAR DENTAL CANALS

BACKGROUND OF THE INVENTION

1. Field of the Invention

The present invention relates to a set of instruments of different diameters for the boring of radicular dental canals, each instrument having a conical stem presenting at least one helicoidal cutting edge.

1. Description of the Prior Art

Such sets of instruments, constituted by files and reamers, are known per se.

The instruments permit a dentist to bore a radicular dental canal by starting with an instrument of small diameter and then using, successively, instruments of increasing diameter until the whole infected pulp is removed and the bored canal has a shape suitable for its obturation by means of gutta-percha or of cement.

Since such instruments have different diameters, the bending moment of each instrument varies from one to another. In the known sets of instruments, this variation of the bending moment follows an exponential curve so that the instruments of small diameter are too flexible while the instruments of larger diameter are too rigid. When an instrument is too flexible, there is a risk of bending even before the dentist has located the opening of the canal while, when the instrument is too rigid, it follows the curve of the dental canal only with difficult manipulation.

SUMMARY OF THE INVENTION

The object of the present invention is to remove the above drawback while furnishing a set of instruments of which the instruments in small diameter are flexible without being too flexible and which the instruments of larger diameter are not too rigid.

The above object is achieved as a result of the shape of the section of the central part of the said which is different from one instrument to another for at least a part of the said instruments, so that the bending moment varies, from one instrument to another, substantially linearly.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilizing the same or equivalent principles may be used, and structural changes may be made as desired by those skilled in the art without departing from the present invention and the purview of the appended claims.

DESCRIPTION OF THE PREFERRED EMBODIMENTS

Figure 1:
FIG. 1 is an elevational view of an instrument for the boring of radicular dental canals.

The instrument shown in FIG. 1 is a part of a set of instruments, which can comprise up to about thirty instruments, each having different diameters. The instrument comprises a cylindrical stem 1 intended to be engaged either into a handle permitting the manual operation of the instruments or into a handle which is itself engaged into a hand-piece ensuring the mechanical driving of the instrument.

The stem 1 is extended by a tapered portion 1$a$ n which are provided cutting edges 2 and which terminates at a conical point 1$b$.

The instrument is formed from a stem of circular section, the front part of which is tapered by working, while providing faces thereon, in such a manner that the tapered portion has a normal section which is polygonal. The stem then is submitted to a torsion to form the helicoidal edges 2. The cutting edges also could be worked into the tapered stem.

The diameter D of the stem at the root of its point 1$b$ comprises the nominal diameter by which the instrument is characterized. It is this nominal diameter, expressed in tenths of millimeters, which is indicated on the X-axis of the diagram of FIG. 5.

In the case of the set of instruments presently disclosed, the general shape of the normal section of the instruments is a square.

However, so far as the instruments of small diameter (FIG. 2) are concerned, the sides 3 of the square of the section of the instrument are constituted by arcs of circles, the convexity of which is turned towards the outside. Hence, the faces of the central part of the instrument, before its torsion or before the working of its cutting edges, are convex as a result, there is an increase of the bending moment $M_f$ of these instruments of small diameter.

Figure 3:
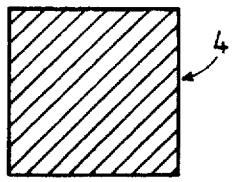

So far as the instruments of middle diameter of the set are concerned (FIG. 3), the sides 4 of the squares constituting the section of these instruments are rectilinear so that the faces of the central portion of the instrument, before its torsion or before the working of its cutting edges, are plane.

Figure 2:
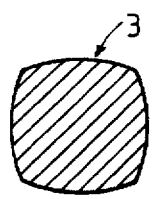
FIGS. 2, 3 and 4 are normal sections, on an enlarged scale than that of FIG. 1, of three instruments of a set of instruments like that of FIG. 1.
Figure 4:
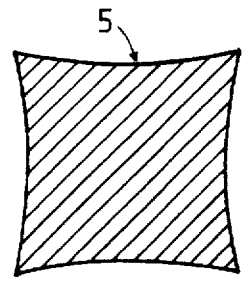

Finally, so far as the instruments of larger diameter of the set (FIG. 4) are concerned, the sides 5 of the squares constituting the normal section of the instruments have the shape of arcs of circles, as in the case of FIG. 2, but, inversely, have their convexity turned towards the inside. Hence, the faces of the central part of the instrument, before its torsion or its working, are concave, which reduces the bending moment of the stems.

Figure 5:
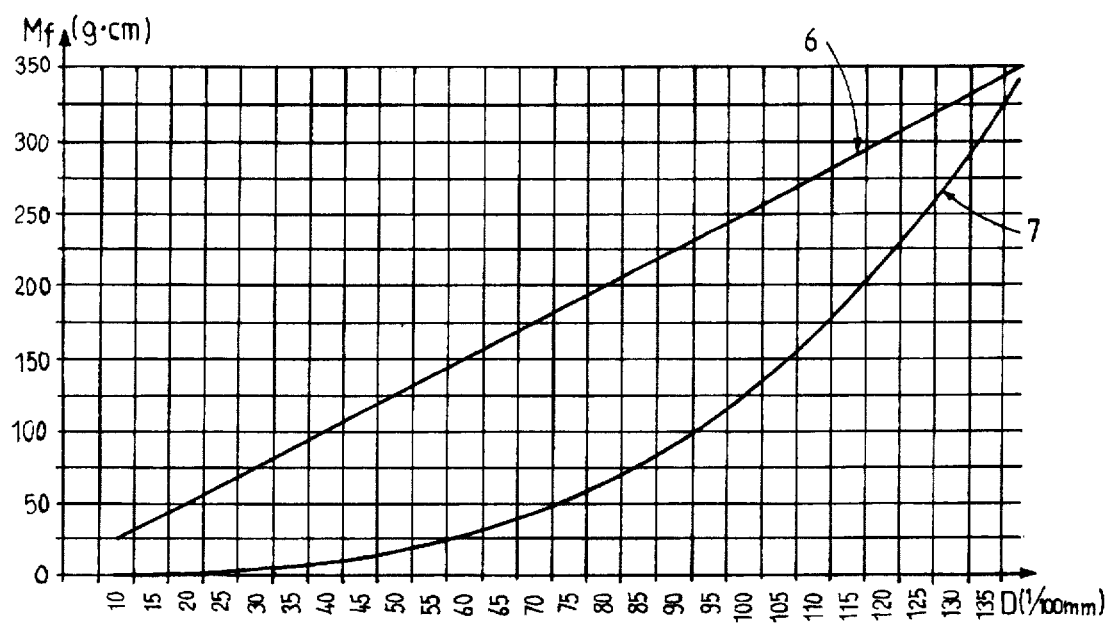
FIG. 5 is a diagram of the bending moments of the instruments of such a set in relation with their diameter, on which diagram also has been indicated the bending moments of the instruments of a known prior art set.

While making a judicious choice of the convexity or of the concavity of the lateral faces of the central part of the instruments, in relation to their diameter, one discovers that the variation of the bending moments $M_f$ of the instruments of the set is linear, as indicated by the curve 6 of the diagram of FIG. 5 where these bending moments are indicated on the Y-axis, expressed in g·cm. The nominal diameters D of the instruments of the set, indicated on the X-axis, are staged from $D_{10}$ ($10/100$ mm) to $D_{140}$ ($140/100$ mm). Obviously, the data indicated in this diagram, either for the bending moments or for the nominal diameters, are only indicative, by way of example, but could vary according to the type of instruments and to the material in which they are made, for example.

The curve 7 appearing on this same diagram indicates the variation of the bending moments of a conventional set of instruments in which the section of the instruments does not vary, so far as its shape is concerned, only the "force" of the instruments varying from one instrument to another. One sees that, in this case, the curve 7 is an exponential, the flexibility of the instruments of the set being steadily lower than the optimum flexibility which is desired, indicated by the curve 6. In this case, if the flexibility of the instruments of small dimension would be increased, this would result in too high rigidity of the instruments of larger dimension.

Theoretically, so that the curve 6 of the diagram of FIG. 5 is perfectly rectilinear, it should be necessary to have, in the set, only one instrument the faces of the central part of which, before the torsion or the working part, is planar. According to FIG. 3 with, all of the other instruments of the set presenting convex faces (FIG. 2) or concave faces (FIG. 4), the convexity and the concavity is different from one instrument to another.

However, as a practical matter, several instruments are provided following each other in the set presenting faces which are planar, of the same convexity or of the same concavity, since the variation Of the bending moment of one instrument to another is relatively small, as shown by the diagram of FIG. 5, when the variation of the nominal diameters in the set is also small, of 5/100 mm from one instrument to the next one.

Figure 6:
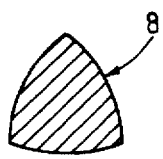
FIGS. 6, 7 and 8 are normal sections, similar to those of FIGS. 2 to 4, of three instruments of a modified set of instruments for the boring of radicular dental canals.
Figure 7:
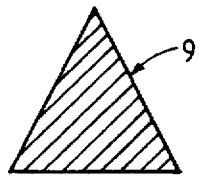
Figure 8:
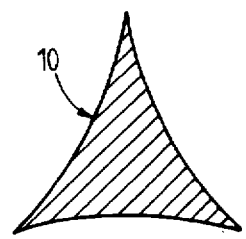

The modification illustrated in FIG. 6, 7 and 8 differs from the first embodiment by the fact that the normal section of the instruments of the set is not of square shape, but of generally triangular shape.

However, as in the case of the first embodiment, the sides 8 of the triangles representing the section of the instruments of small dimension are arcs of circles, their convexity being turned towards the outside. The sides 9 of the triangles of the instruments of middle dimension are rectilinear and the sides 10 of the instruments of larger dimension are arcs of circles, the convexity of which is turned towards the inside, so that the variation of the bending moments is substantially linear.

The section of the central part of the instruments of the set could be different from a square or from a triangle as disclosed and represented, while remaining polygonal.

I claim:

1. A set of instruments for boring radicular canals comprising, the instruments being of different diameters with respect to each other, each instrument having a conical stem with at least one helicoidal cutting edge and a central part, the configuration of a section taken through the central part of each instrument being different from one instrument to another and varying from small to intermediate to larger, whereby the bending moment of each instrument varies substantially linearly from one instrument to another.

2. A set of instruments as claimed in claim 1 in which said section is of generally polygonal configuration, the sides of the poloygon of said polygonal configuration being convex for the instruments of small section, rectilinear for the instruments of intermediate section, and concave for the instruments of larger section.

* * * * *